United States Patent [19]

Yiu et al.

[11] Patent Number: 4,721,679
[45] Date of Patent: Jan. 26, 1988

[54] TISSUE TYPING TRAY

[76] Inventors: Felix H. F. Yiu, 8600 Mason Ave., Canoga Park, Calif. 91306; Jimmy Loon, 6931 Garden Grove Ave., Reseda, Calif. 91335

[21] Appl. No.: 922,207

[22] Filed: Oct. 23, 1986

[51] Int. Cl.<sup>4</sup> ............................................. C12Q 1/20
[52] U.S. Cl. .................................. 435/301; 220/23.8; 220/359
[58] Field of Search ............... 435/300, 301, 285, 293, 435/298, 284, 286; 436/809; 220/23.8, 359, 256

[56] References Cited

U.S. PATENT DOCUMENTS

| | | | |
|---|---|---|---|
| 3,055,808 | 9/1962 | Henderson | 435/301 |
| 3,107,204 | 10/1963 | Brown et al. | 435/298 |
| 4,030,980 | 6/1977 | Beckford et al. | 435/301 |
| 4,599,315 | 7/1986 | Terasaki et al. | 435/301 |

Primary Examiner—Samuel Scott
Assistant Examiner—Noah Kamen
Attorney, Agent, or Firm—Cislo & Thomas

[57] ABSTRACT

A tissue typing tray is provided with an improved well cover. The tissue typing tray is of conventional box-like construction, with conjoining side walls and a bottom and a plurality of wells disposed on the bottom. The well cover comprises a flat member, with a downwardly depending, continuous ridge member inwardly spaced from the perimeter of the flat member and terminating in a flat surface provided with a pressure sensitive adhesive thereon. The ridge member is of the same height as the wells and encompasses the wells. Upon engagement of the well cover with the tissue typing tray, the adhesive-coated ridge member contacts the bottom of the tray, while the flat member of the well cover contacts the tops of the wells. The sealing configuration of the well cover prevents its lateral or vertical movement, thereby preventing possible loss of testing reagent from the wells or contamination of the contents of one well by the contents of another. An optional top cover comprises a flat cover member and a downwardly depending, continuous side wall member around the perimeter thereof for releasable friction-fit engagement with the exterior of the side walls of the tissue typing tray.

11 Claims, 5 Drawing Figures

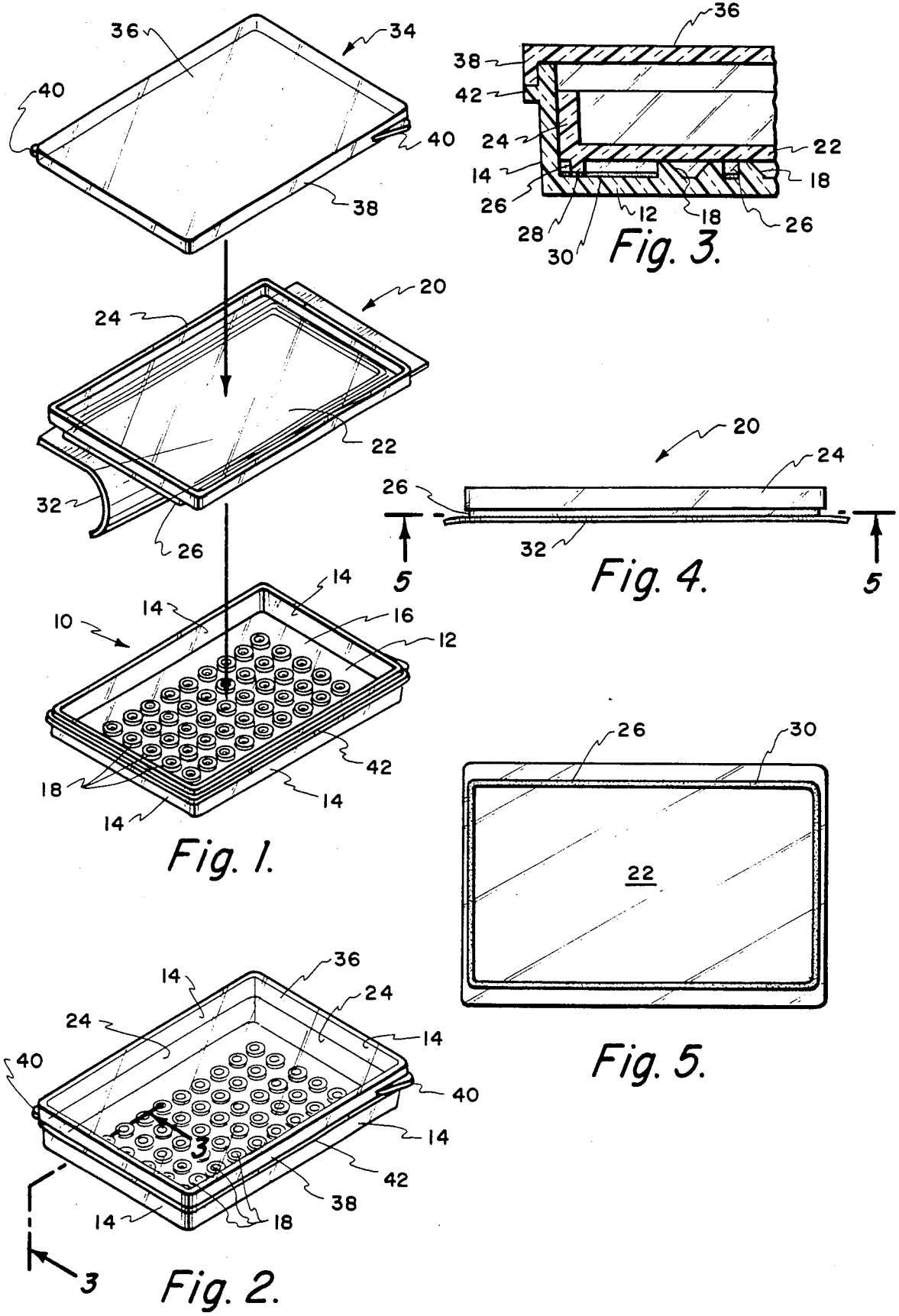

TISSUE TYPING TRAY

BACKGROUND OF THE INVENTION

1. Field of the Invention

The present invention relates to tissue typing trays of the type provided with a plurality of wells for microcytotoxic testings and analysis, and, more particularly, to an improved closure for such trays.

2. Description of Related Art

Tissue typing trays typically comprise a box-like construction of conjoining side walls and a bottom, with a plurality of wells disposed on the bottom in an array. Solutions may be introduced into the wells, and testing perform therein. The wells are usually sealed by melting wax around the perimeter of the wells and sealing a well cover thereto in order to prevent evaporation and contamination from the external environment. It also protects user from contents on the tray. A tray cover engages the tops of the side walls in snap-fit closure.

However, the well cover is easily movable laterally, resulting in potential loss of testing reagent and in possible contamination of the contents of one well by the contents of another.

OBJECTS AND SUMMARY OF THE INVENTION

Accordingly, it is an object of the present invention to provide a well cover which may be secured to the tissue typing tray in a laterally immobile position.

It is another object of the present invention to provide a well cover which may be secured to the tissue typing tray in a manner so as to prevent loss of testing reagent or possible contamination of the contents of one well by the contents of another or contamination or infecting personnel by leakage.

It is yet another object of the present invention to provide a well cover which may be secured to the tissue typing tray having an optical clarity to permit microscopic examination of the contents of the wells.

It is a still further object of the present invention to provide a well cover which may be secured to the tissue typing tray in a manner so as to permit attachment of an optional top cover to the tissue typing tray.

These and further objects of the invention will become more readily apparent upon a consideration of the following commentary taken in conjunction with the appended drawings.

Briefly, a tissue typing tray, which comprises a box-like construction of conjoining side walls and a bottom, with a plurality of wells disposed on the bottom in an array and extending upwardly a given height from the bottom, is provided with a well cover which may be secured to the bottom of the tray. The well cover comprises a flat cover member having two opposed major surfaces. Inwardly spaced around the perimeter of the second major surface is a downwardly depending, continuous ridge member. The ridge member terminates in a flat surface which is provided with an adhesive and is of a height substantially equal to that of the wells.

Sealing of the wells is accomplished by engaging the adhesive-coated ridge member with the bottom surface of the tray, thereby urging the second major surface against the tops of the wells. A removable top cover may be optionally provided, which engages the outside of the side walls of the tissue typing tray in releasable friction-fit relationship.

The sealing relationship of the well cover of the invention prevents vertical or lateral movement of the well cover. Accordingly, the contents of each well are maintained therein, and possible contamination of the contents of one well by the contents of another well is prevented.

BRIEF DESCRIPTION OF THE DRAWINGS

FIG. 1 depicts, in perspective view, the assembly of the tissue typing tray of the invention, showing the tray with its plurality of wells, the well cover, and an optional top cover;

FIG. 2 is a perspective view of the assembled tissue typing tray of FIG. 1;

FIG. 3 depicts, in cross-section, a portion of the assembled tissue typing tray, taken along the line 3—3 of FIG. 2;

FIG. 4 is a side elevational view of the well cover of the invention, with a removable adhesive-protecting medium in place prior to removal; and FIG. 5 is a bottom plan view of the well cover of FIG. 4, with the adhesive-protecting medium removed.

DETAILED DESCRIPTION OF THE PREFERRED EMBODIMENTS

Referring now to the drawings wherein like numerals of reference designate like elements throughout, a tissue typing tray 10 comprises a bottom 12 and a plurality of conjoining side walls 14, typically four such side walls, defining an enclosure 16, typically rectangular. A plurality of wells 18 is disposed in an array on the bottom 12 of the tissue typing tray 10. The dimensions (height and inner diameter) and formation of the wells 18 are those well-known in the prior art and do not form a part of this invention.

A well cover 20 is fixedly attached to the bottom 12 of the tray 10. The dimensions of the well cover 20 are operatively associated with those of the tissue typing tray 10.

The well cover 20 further comprises a downwardly depending, continuous ridge member 26 which is slightly spaced inwardly from the perimeter of the cover member 22. The ridge member 26 is of substantially the same height as that of the wells 18. The ridge member 26 terminates in a flat surface 28, which is provided with a layer of an adhesive 30. The adhesive 30 is protected until use by a conventional removable protective medium 32. The inward spacing of the ridge member 26 is not particularly critical, other than it totally encompasses the array of wells 18.

An optional top cover 34 comprises a flat cover member 36 and a downwardly depending, continuous side wall member 38 that extends around the perimeter of the cover member and is sized to encompass the outside of the side walls 14 of the tray 10 in releasable friction-fit reltionship. A pair of opposed tabs 40 aid in removing the top cover 34. A ledge member 42 on the exterior of the side walls 14 of the tissue typing tray 10 provides a stop for the bottom of the side wall member 38 of the top cover member 34.

The various parts (tray 10, well cover 22, and optional top cover 34) preferably comprise a crystal polystyrene, such as that available under the trademark "Lustrex" by Monsanto Chemical Co. (St. Louis, Mo.). Such material has the high optical transmission required for microscopic analysis of tissue testings, is easily formed into the required shapes with a minimum of mold shrinkage, and has high strength and durability.

The adhesive employed is a pressure sensitive adhesive. An example of a suitable adhesive is available from 3M Company under the trademark "Scotch-Grip" No. 4268. This adhesive may be used with the high impact polystyrene material above and is a water-based material.

In operation, the wells 18 are filled with testing reagents, as is conventional. The protective medium 32 on the adhesive portion 30 of the well cover 20 of the invention is removed, and the well cover is inserted into the tray 10 until the bottom surface 28 of the ridge 26 contacts the bottom 12 of the tray. The adhesive 30 holds the well cover 20 in place, preventing vertical movement of the well cover. The bottom surface of the cover member 22 makes sealing contact with the tops of the wells 18, thereby preventing loss of the testing reagent from the wells.

Use of the well cover 20 of the invention permits closer spacing of the wells 18 than permissible with prior art well covers. Consequently, more wells may be formed in a tissue typing tray 10 of the same outer dimensions than in the prior art.

As an example, 72 wells are formed in a 6×12 array, disposed on the bottom 12 of a tissue typing tray 10. For comparison, a prior art tray has 60 wells formed in a 6×10 array. Both the prior art tray and the tray of the invention have outside dimensions of 5.4×8.0 cm. Thus, it will be appreciated that the cover of the invention permits closer spacing of wells than available with prior art trays. Consequently, more wells (for example, 20% more) may be placed in the same tray size than by the prior art as a result of the sealing contact between the cover member 22 and the wells 18 and as a result of the immovability of the well cover 20.

Thus, there has been disclosed a tissue typing tray with an improved cover. Various modifications and changes will make themselves available to those of ordinary skill in the art, and all such changes and modifications not deviating from the spirit and esssence of the invention are intended to be covered by the appended claims.

What is claimed is:

1. A well cover in combination with a tissue typing tray, said tray comprising a box-like construction of conjoining side walls and a bottom, with a plurality of wells provided in an array on said bottom and extending upwardly therefrom to a predetermined height, said cover comprising a flat cover member having two opposed major surfaces, with a downwardly depending, continuous ridge member inwardly spaced around the perimeter of a second major surface, said ridge member terminating in a substantially flat surface coated with an adhesive, the height of said ridge member being substantially equal to that of said wells, said adhesive-coated surface of said ridge member being designed for sealable contact with said bottom of said tray around said array of said wells, and said second major surface of said well cover being designed for contact with the tops of said wells in sealing configuration.

2. The well cover of claim 1 wherein said well cover comprises crystal polystyrene.

3. The well cover of claim 1 wherein said adhesive comprises a water-based pressure sensitive adhesive.

4. The well cover of claim 1 wherein a removable protective medium overlies said adhesive prior to engagement of said well cover in said tissue typing tray.

5. The well cover of claim 1 wherein said tissue typing tray and said well cover have matching rectangular configurations.

6. A tissue typing tray and well cover combination, wherein said tissue typing tray comprises a box-like construction defined by conjoining side walls and a bottom, with a plurality of wells provided in an array on said bottom and extending upwardly therefrom to a predetermined height, said well cover comprising a flat cover member having two opposed major surfaces, with a downwardly depending, continuous ridge member inwardly spaced around the perimeter of a second major surface, said ridge member terminating in a substantially flat surface, the height of said ridge member being substantially equal to that of said wells said substantially flat surface of said ridge member being adhesively bonded to said bottom of said tray around said array of said wells, and said second major surface of said well cover being in contact with the tops of said wells in sealing configuration.

7. The combination of claim 6 wherein said tissue typing tray and said well cover comprise crystal polystyrene.

8. The combination of claim 6 wherein said adhesive comprises a water-based pressure sensitive adhesive.

9. The combination of claim 6 wherein said tissue typing tray and said well cover have matching rectangular configurations.

10. The combination of claim 6 wherein a top cover is provided for releasable friction-fit engagement of the exterior of said side walls of said tissue typing tray, said top cover comprising a flat cover member and a downwardly depending, continuous side wall member around the perimeter thereof.

11. The combination of claim 10 wherein said top cover comprises crystal polystyrene.

* * * * *